United States Patent
Stock et al.

(10) Patent No.: US 9,188,534 B2
(45) Date of Patent: Nov. 17, 2015

(54) DEVICE WITH A MEASUREMENT ARRANGEMENT FOR OPTICAL MEASUREMENT OF GASES AND GAS MIXTURES, WITH COMPENSATION OF ENVIRONMENTAL EFFECTS

(75) Inventors: Burkhard Stock, Lübeck (DE); Nils Haack, Lübeck (DE); Wilfried Diekmann, Utecht (DE); Björn Lange, Teschow (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 0 days.

(21) Appl. No.: 14/130,512

(22) PCT Filed: Jul. 2, 2012

(86) PCT No.: PCT/EP2012/062843
§ 371 (c)(1),
(2), (4) Date: Jan. 2, 2014

(87) PCT Pub. No.: WO2013/004664
PCT Pub. Date: Jan. 10, 2013

(65) Prior Publication Data
US 2014/0124672 A1    May 8, 2014

(30) Foreign Application Priority Data
Jul. 2, 2011    (DE) .................... 20 2011 102 765 U

(51) Int. Cl.
| G01N 21/61 | (2006.01) |
| G01N 21/03 | (2006.01) |
| G01N 21/09 | (2006.01) |
| G01N 21/15 | (2006.01) |
| G01N 21/31 | (2006.01) |
| G01N 21/3504 | (2014.01) |

(52) U.S. Cl.
CPC .............. *G01N 21/61* (2013.01); *G01N 21/031* (2013.01); *G01N 21/0332* (2013.01); *G01N 21/09* (2013.01); *G01N 21/15* (2013.01); *G01N 21/314* (2013.01); *G01N 21/3504* (2013.01)

(58) Field of Classification Search
CPC ........................... G01N 21/3504; G01N 21/61
USPC ........................................................ 250/343
See application file for complete search history.

(56) References Cited

U.S. PATENT DOCUMENTS 5,886,348 A  *  3/1999  Lessure et al. ........... 250/339.13
5,923,035 A       7/1999  Winkler et al.
(Continued)

FOREIGN PATENT DOCUMENTS

| CN | 100552433 C | 10/2009 |
| WO | 2006068781 A2 | 6/2006 |
| WO | 2010118748 A1 | 10/2010 |

*Primary Examiner* — Marcus Taningco
(74) *Attorney, Agent, or Firm* — McGlew & Tuttle, P.C.

(57) ABSTRACT

A device for optical detection of a target gas in gas mixtures includes an operation and evaluation unit, a measurement cuvette with optically reflective surfaces on its interior walls and a gas inlet to the environment, a radiation source, a measuring detector and a reference detector unit provided on the measurement cuvette. The measuring detector and the reference detector unit detect the light of the radiation source and produce electrical signals corresponding to the intensity of the detected light. An optical bandpass filter element, constructed to transmit light of a measurement wavelength, is arranged upstream of the measuring detector. An optical double-bandpass filter unit, that transmits light of a first reference wavelength and light of a second reference wavelength, is arranged upstream of the reference detector unit. The operation and evaluation unit operates the radiation source and acquires the electrical signals of the measurement detector and the reference detector unit.

20 Claims, 5 Drawing Sheets

(56) References Cited

U.S. PATENT DOCUMENTS

| | | |
|---|---|---|
| 6,455,854 B1 | 9/2002 | Richman |
| 6,469,303 B1 | 10/2002 | Sun et al. |
| 7,034,304 B2 * | 4/2006 | Tice et al. ............... 250/343 |
| 7,285,782 B2 | 10/2007 | Schubert |
| 7,301,640 B2 * | 11/2007 | Tice ............... 356/437 |
| 7,406,854 B2 | 8/2008 | Lange et al. |

* cited by examiner

DEVICE WITH A MEASUREMENT ARRANGEMENT FOR OPTICAL MEASUREMENT OF GASES AND GAS MIXTURES, WITH COMPENSATION OF ENVIRONMENTAL EFFECTS

CROSS REFERENCE TO RELATED APPLICATIONS

This application is a United States National Phase Application of International Application PCT/EP2012/062843 filed Jul. 2, 2012 and claims the benefit of priority under 35 U.S.C. §119 of German Utility Model DE 20 2011 102 765.5 filed Jul. 2, 2011, the entire contents of which are incorporated herein by reference.

FIELD OF THE INVENTION

The present invention pertains to a measurement arrangement for the infrared optical measurement of gases and gas mixtures with compensation of environmental effects.

BACKGROUND OF THE INVENTION

The possibility for analyzing gas mixtures is an essential boundary condition in the monitoring of industrial plants for an incident-free and safe operation, especially against the background of the increasing degree of automation. To make it possible to recognize gases escaping in case of an incident as accurately and rapidly as possible, for example, in major industrial plants, in petrochemical plants or on drilling platforms, it is desirable to detect the discharge of gases that are hazardous for health even at low concentrations with a high measuring sensitivity directly at the sites of possible incidents.

Optical gas detector systems are especially suitable for detecting low concentrations with a high measuring sensitivity.

Optical gas detector systems, which are arranged as selected measuring stations at a plurality of measurement points in a defined area in an industrial plant or are arranged distributed in a large area, are known from the state of the art.

These optical gas detector systems with optical point detectors comprise a light source, a measuring cuvette penetrated by the light, a narrow-band optical filter and a detector for measuring the light intensity. Absorption of light by the gas to be measured leads to a reduced detector signal, which is analyzed as a measured variable.

Furthermore, gas measurement systems, with which gas concentrations of larger areas or surfaces are detected, are known from the state of the art. Such systems comprise a transmitter with a light source and with a directed receiver with detector, as well as additional optical elements for guiding the light beam. The light beam passes over distances in the range of a few m up to 50 m, 200 m or even more as an optical measured section from the transmitter to the receiver. Such a measuring unit, also called open-path measurement system, is shown in U.S. Pat. No. 6,455,854.

An arrangement with a measuring cuvette communicating with the ambient gas is described in U.S. Pat. No. 5,923,035. The measuring cuvette forms an optical measured section between a light source and a detector. The mean path traveled by the light beam in the cuvette determines the optical measured section and hence the optical path length of the measurement arrangement, the arrangement being able to be selected to be an arrangement in which the light source and the detector are arranged directly opposite each other. One mirror or a plurality of mirrors may be arranged for beam deflection or for extending the optical path length in an arrangement in which the light source and the detector are arranged on the same side for reasons of construction, or the walls of the cuvette may be made or arranged such that they reflect light, such that this leads to mirroring and/or multiple reflections in the cuvette, which extends the optical path length from the light source to the detector. Cuvettes designed in this manner are also called multi-reflection cuvettes in the state of the art. Such multi-reflection cuvettes are made completely reflecting on the inner side of the wall in the overwhelming majority of embodiments, so that part of the quantity of light emitted in an undirected manner reaches the detector over a longer path due to multiple reflections on the wall when a radiation source with undirected light beam is used. Another part of the quantity of light reaches, reflected only once, the detector over a shorter path. An arrangement for a locally limited measurement at a measurement point according to U.S. Pat. No. 5,923,035 is called a so-called point detector, for distinction from an open-path arrangement according to U.S. Pat. No. 6,455,854, because locally limited measurements can be carried out with such a measurement arrangement. An industrial area can be purposefully and specifically monitored, for example, via a spatially distributed array of a plurality of such point detectors at a plurality of measurement points. A special form of such point detectors is a mobile manual measurement device for measurement tasks that are limited in space, i.e., selected measurement tasks, with the special feature that the measurement point can be selected by the user as a variable and mobile measurement point.

The intensity of the light beam detected at the detector, which intensity can be measured by the measurement arrangement, is determined by the absorption properties of the gas or gas mixture present in the cuvette and the length of the optical path length. The presence and the concentration of certain gas components or gas species in the area of the measured section can be inferred from the spectrum detected and the signal intensity of individual wavelengths in the spectrum in a very precise manner.

Depending on the measurement task, the optical path length is determined by the structural conditions of the measurement environment. In a measurement arrangement for use in a locally limited single-point measurement for concentration measurement, the structural conditions, such as the dimensions of the housing and the length of the cuvette, preset the optical path length in a range of a few cm, for example, in a range of 3 cm to 23 cm. Besides the optical path length as twice the overall length of the cuvette in case of the use of a radiation source with undirected light beam, further optical paths are obtained statistically due to the multiple reflection in measurement arrangements with multi-reflection cuvettes, in which the light is emitted, originating from the radiation source, into the cuvette, is reflected on the opposite wall and on the lateral walls and reaches the detector arranged next to the radiation source. A mean optical path length is thus obtained, which is greater than that determined by the actual overall length. For example, in case of an overall cuvette length with an inner dimension of 5 cm, an effective optical path length of 7 cm to 50 cm is obtained, depending on the construction and the reflection properties of the multi-reflection cuvette. In an application for concentration measurement by means of an open-path measurement system in the free field, the optical path length is in the range of a few m to more than 50 m and up to 200 m or even more.

These structural conditions lead to design criteria and selection criteria for the selection of a suitable measurement wavelength M for a high-resolution and specific measurement of the concentration of a certain gas. It is desirable, in principle, for the highest sensitivity possible to be present over the entire measuring range in the presence of a concentration of the target gas in the gas mixture.

Furthermore, multireflection cuvettes are advantageous in the sense that no collimated light beam is necessary as a light source, unlike in an open-path free field arrangement according to U.S. Pat. No. 6,455,854, in which the light source (transmitter) and detector (receiver) must be exactly aligned with one another and the light beam per se is aligned, for example, by a laser light source, or additional optical components, such as lenses and/or mirrors are present for focusing, guiding and deflecting the light in case of using a light source without a limited beam collimation in the light source itself. Multireflection cuvettes are especially advantageous for practical use because, unlike in the case of a construction with mirror elements as an individual reflection point in case of contamination of the only mirror element, measurement still continues to be possible in case of partial contamination of the reflecting surfaces in the cuvette. This insensitivity to locally limited local contaminations arises from the fact that since the light is coupled from the light source into the multireflection cuvettes in the undirected form, statistically locally random and varying reflections occur on the reflecting surfaces, both as single, double and even multiple reflections, before the light reaches the detector. As a result, a locally limited local contamination does not become an effective drawback for the gas concentration measurement due to the statistically random and continuously varying reflections.

In a practical implementation with a measuring range of interest for monitoring explosion limits of a target gas, it is advantageous that, for example, the presence of a target gas in the measuring cuvette with a concentration corresponding to the lower explosion limit brings about light absorption, which causes a reduction of the signal at the detector in the range of about 10% to 15%, for example, for the target gas methane. Furthermore, the most uniform rise possible of the characteristic curve of the light absorption or of the reduction of the signal at the detector over the measuring range of interest is desirable. This leads, on the one hand, to a marked measurement effect due to the target gas, and, on the other hand, further light absorption due to cross sensitivities to other gases and the effect of environmental conditions, such as temperature fluctuations, effect of air pressure and effect of moisture, can be accepted, without the light being able to be absorbed, for example, by water of condensation almost completely at the optical path length.

To make it possible to achieve this design criterion concerning the light absorption, measurement wavelengths specifically suitable for the measured gas are to be selected in combination with suitable optical path lengths.

To make it possible to measure low concentrations with high measuring sensitivity, it is necessary to adapt the construction of the measurement arrangement and the adaptation of the components of the measurement arrangement to the measurement task and to the environmental conditions for the operation of the measurement arrangement very accurately. It is essential for high sensitivity of the measurement and for specific selectivity for certain target gases that the measurement wavelength be selected for the target gas and for the optical path length of the measured section in the cuvette. The overall size of the cuvette is preset essentially by the space available for installing the gas-measuring device, but the space available for installation has its limitations for mobile gas-measuring devices concerning applicability for mobile applications. The length of the measured section within the cuvette is limited, on the one hand, by the losses of light over the measured section itself and the light absorption by the target gas, and further essential limitations arise from the losses that occur due to the optical components and are due to the sensitivity of the detector used.

The possibility of distortions of the measurement due to environmental conditions such as cold, heat and humidity is an essential parameter affecting the precision of the measurement arrangement. The moisture in the cuvette can be reduced, in principle, in case of use in a moist measurement environment by reducing the relative humidity within the cuvette and by preventing condensation on the walls of the cuvette as well as on the light source and detector.

Heating of the optical system is a known and effective method for this according to the state of the art, as this is described, for example, in U.S. Pat. No. 7,406,854.

Such heating is not quite uncritical for using the measurement arrangement in areas with explosion hazard. To prevent an explosion of the possibly explosive gas present in the environment due to possible electric sparks or an energy discharge in the measurement arrangement, it is absolutely necessary to design the measurement arrangement such that no sparks or critical quantity of energy, which could cause ignition of a gas mixture in the measurement environment, can pass over from the measurement arrangement into the measurement environment. Furthermore, if no explosion occurs in the measurement arrangement proper, the explosion must remain limited to the measurement arrangement and must not pass over or flash over into the measurement environment. The entry of gas from the measurement environment to and into the measuring cuvette is designed in a specially secured manner for this by means of a protective element. The entry of gas is provided with a special protective element in such an explosion-proof design.

A gas sensor of an explosion-proof design is known from U.S. Pat. No. 7,285,782, wherein the gas exchange takes place via a gas exchange opening, which is provided with a dust filter consisting of a sintered material or a metal gauze and with a moisture protection filter as a protective element.

In an expanded embodiment, the gas sensor described in U.S. Pat. No. 7,285,782 has an infrared detector with at least one gas-specific measuring channel 1, 2, 3, as well as a reference channel 0, which has a zero signal, i.e., a signal that is not affected by the target gas. To take into account and compensate environmental effects, a temperature sensor, a moisture sensor and a pressure sensor are additionally provided at the infrared detector.

Despite a protective element at the gas outlet opening, heating for the measurement arrangement may be carried out with a moderate quantity of energy only in the explosion-proof design, so that, for example, a temperature rise of 5° C. to 10° C. relative to the ambient temperature is reached. A temperature rise by 10° C. in the measuring cuvette at an ambient temperature of 10° C. and a relative air humidity of 100% causes a reduction of the relative humidity of the air to about 70% to 80%, so that condensation is prevented from occurring. Any reduction in the relative humidity of the air in the measuring cuvette brings about, in principle, a reduction of the impairment of the measurement by water of condensation or droplets of water in the cuvette.

Measurement tests have revealed that measurement is affected especially in measurement arrangements for the infrared optical measurement of gases and gas mixtures in case of a design embodiment as multireflection cuvettes of an explosion-proof design with a protective element and despite heating if the measurement arrangement was exposed to a moist measurement environment during the operation before or is exposed now to such a moist measurement environment.

A solution concerning avoiding condensation for a measurement arrangement of a non-explosion-proof design can be obtained in a simple manner by markedly intensifying the heating and heating the measuring cuvette as a result to the extent that the relative humidity of the air in the measuring cuvette will be reduced to values between 5% and 10% relative air humidity. The consequence of this is always an undesired, high energy consumption for such a measurement arrangement.

Any increase in the heat output during the operation is associated, however, with the drawback for mobile devices, of both an explosion-proof design and a non-explosion-proof design, that the quantity of electric energy needed therefore must be carried along additionally in the form of an energy storage device (batteries rechargeable batteries), which would result in a disadvantageous excess weight for mobile applications, or that the available operating time becomes shorter for mobile application without increasing the weight of the device, which is not realistic in case of the application scenarios of mobile gas-measuring devices in practical use.

The explosion protection measures must be massively intensified for a measurement arrangement of an explosion-proof design, which is likewise associated again with drawbacks for the mobile use, besides a globally increased weight and volume, and additionally also has consequences for the construction and design of the protective element at the gas inlet. This protective element, made of sintered material, sintered metal or metal gauze, must be designed structurally, like the other components of the housing of the measurement arrangement as well, such that the quantity of energy made available for the heating can be retained in the measurement arrangement in case of an incident. This circumstance leads to a very massive construction for the protective element, which makes the access of gas difficult and causes disadvantageous changes in the measurement properties, and, in particular, the response characteristic in case of a gas exchange, usually characterized by the so-called t10-90 time, is adversely effected by the longer diffusion time of the gas through the protective element, which is now necessary, in such a way that the warning function of the measurement arrangement will not occur with a short delay after a change in concentration in the measurement environment. The t10-90 time is defined for a gas-measurement arrangement as the time needed for detecting, outputting and displaying a change in the gas concentration from 10% of a target gas concentration to 90% of a target gas concentration. Further difficulties arise in the embodiment for the use of the measurement arrangement in areas with explosion hazard, because the quantity of energy being carried along and the temperatures of elements in the measurement arrangements are limited by regulatory requirements.

Thus, it is not possible in a practical embodiment to prevent condensation nearly completely by means of increasing the heat output while bringing about a marked reduction of the relative humidity of the air in the measuring cuvette to values between 5% and 10% for both a measuring cuvette of non-explosion-proof design and a measuring cuvette of an explosion-proof design.

A device and a method for compensating environmental effects by means of two reference wavelengths is described for an open-pass measuring system with an optical path length of one meter to one thousand meters in U.S. Pat. No. 6,455,854. A wavelength range of 2,100 nm to 2,400 nm with one measurement wavelength and two reference wavelengths, which range is suitable for the optical path length of one meter to one thousand meters, is used here for the measurement of alkanes. The reference wavelengths are characterized in that they are not subject, in principle, to any effect of the measured gas or other gases of the measurement environment. At 2,300 nm, the measurement wavelength is selected essentially in the middle between a first reference wavelength R1 at 2,215 nm and a second reference wavelength R2 at 2,385 nm. According to U.S. Pat. No. 6,455,854, the effect of fog and rain on the absorption at the measurement wavelength is compensated by the effect at the first reference wavelength R1 with the effect at the second reference wavelength R2 having the same effect as the effect at the measurement wavelength.

The wavelengths selected in U.S. Pat. No. 6,455,854 (2,215 nm, 2,300 nm, 2,385 nm) are suitable, according to U.S. Pat. No. 6,455,854, for optical measured sections with lengths ranging from one to a thousand m. Due to this length, the absorption of the IR light by the target gas is high enough to obtain a metrological effect.

The wavelengths selected in U.S. Pat. No. 6,455,854 (2,215 nm, 2,300 nm, 2,385 mm) are thus suitable for the metrological monitoring of large areas with an open measured section (open path). The light-emitting light source (transmitter) and the light-receiving detector (receiver) or the light-receiving detectors (receivers) are arranged at great distances from each other in space (1 m<l<1,000 m), ranging from a few m to a thousand m in an open-path measuring system according to U.S. Pat. No. 6,455,854.

The wavelengths selected in U.S. Pat. No. 6,455,854 (2,215 nm, 2,300 nm, 2,385 nm) are less suitable for substantially shorter optical measured sections, as they are used in measuring devices with a closed optical measured section (1<0.3 m), in which the light-emitting light source (transmitter) and the light-receiving detector (receiver) or the light-receiving detectors (receivers) are arranged close next to each other together in a measuring cuvette as point detectors with an optical measured section shorter than 0.3 m, because the absorption of the IR light by the target gas over the optical measured section (1<0.3 m) is not high enough at these wavelengths to achieve an appreciable measurable and useful effect to detect, for example, a lower explosion limit (LEL) with the required accuracy. The consequence of this is that these wavelengths (2,215 nm, 2,300 nm, 2,385 nm) are unsuitable for a measurement arrangement designed as a point detector for the measurement of alkanes by means of a cuvette, whose effective optical path length is markedly shorter than 30 cm due to the overall size.

The combination of a moisture effect with a salt effect occurs as a special environmental effect during operation especially in a maritime environment. The ambient air additionally contains very fine salt crystals, besides the moisture, e.g., on an offshore drilling platform or onboard ships. These salt crystals enter the measuring cuvette in the form of an aerosol and are deposited as a very thin crystalline salt film on the inner walls of the measuring cuvette, as well as on the optical components, such as lenses, filters and mirrors.

This salt film has a hygroscopic action and causes more moisture to be "drawn into" the measuring cuvette continually from the measurement environment after a single-time contamination with salt-containing aerosol. The degree of relative humidity itself is determined by the intrinsic heating by the radiation source and can be reduced by an additional heating of the detector and/or of the cuvette to values in the range of 80%, so that contamination with the formation of larger drops of water on the optical components and on the inner walls of the cuvette can then be avoided. It is ensured hereby that the measurement arrangement does not become "optically blind." The term "optically blind" means in the sense of the present invention that a reflection does not occur any more on the optical elements provided for that purpose during the operation.

Due to the hygroscopic properties of the crystalline salt film, moisture is drawn into the measuring cuvette from the measurement environment, which represents a nearly permanent operating situation with atmospheric humidity in the measuring cuvette following a single-time contamination by salt-containing ambient air. This permanent operating situation determines the measurement conditions for the measurement properties of the measurement arrangement over rather long periods of time ranging from months to years as a measurement condition with the continuous presence of atmospheric humidity in the measuring cuvette, and only the formation of condensation and droplets of water on the walls of the cuvette and the optical components, such as lenses, filters and mirrors can be prevented by heating, but the continuous presence of atmospheric humidity at variable and unknown concentrations cannot. This atmospheric humidity does affect the light absorption at the measurement wavelength and hence the possibility of metrologically detecting the target gas concentration and the metrological precision and reproducibility of such detection.

Furthermore, the ambient air frequently contains further components which can adhere with the water film to the surfaces of the cuvette, to the detectors and the optical elements in many areas of application.

Combustion residues of fossil fuels, such as smoke and soot particles, may be mentioned as such other components of the ambient air, especially in an ambient air with high atmospheric humidity, for example, fog. The effect of these environmental effects, especially of the continual, further supply of atmospheric humidity into the cuvette by the crystalline hygroscopic salt film, cannot be compensated by heating alone, especially for a measurement arrangement of an explosion-proof design in scenarios of use such as offshore drilling platforms or onboard ships.

The continual penetration of atmospheric humidity into the cuvette due to the hygroscopic effect of the fine crystalline salt films cannot be fully compensated even for a measurement arrangement of a non-explosion-proof design by changing the heating of the detector and/or cuvette, e.g., by increasing the heat output or by raising the heating temperature or even by a cyclically performed heating of the entire measurement arrangement.

These environmental effects likewise cannot be fully compensated either by the use of additional sensors, such as temperature, moisture and pressure sensors in the cuvette or at the detectors.

SUMMARY OF THE INVENTION

An object of the present invention is therefore to make available a measurement arrangement for a locally limited infrared optical measurement of gases and gas mixtures with compensation of environmental effects, especially for compensating the effect of moisture.

According to the invention, a device is provided for the optical detection of a target gas in gas mixtures. The device comprises an operating and analyzing unit, a measuring cuvette, which is designed as a multireflection measuring cuvette with optically reflecting surfaces on the inner walls and has a gas inlet, which is designed to exchange gases and gas mixtures with a measurement environment, a radiation source, which emits light into the measuring cuvette, a measuring detector, provided at the measuring cuvette and a reference detector unit provided at the measuring cuvette. The measuring detector and the reference detector unit are designed to detect the light of the radiation source and to convert it to (provide an output/produce) electrical signals, which correspond to the intensity of the detected light. An optical band pass filter element, which is designed to transmit light of a measurement wavelength, is arranged in front of the measuring detector. An optical double band pass filter unit, which is designed to transmit light of a first reference wavelength and light of a second reference wavelength, is arranged in front of the reference detector unit. The operating and analyzing unit is designed to operate the radiation source and to detect the electric signals of the measuring detector and of the reference detector unit.

The following components are provided in and at a measuring cuvette and are present at a measuring site or in the vicinity of the measuring site according to the present invention in a device for the optical detection of a target gas with compensation of environmental effects, especially for compensating the effect of moisture:

a radiation source, which is designed to emit light in the infrared spectrum, preferably in an infrared wavelength range of 2,000 nm to 5,000 nm and more preferably in a wavelength range of 3,000 nm to 4,000 nm;

a measuring detector, which is designed to detect the of the radiation source and to convert it into electrical signals, which correspond to the intensity of the detected light;

at least one reference detector, which is designed to detect the light of the radiation source and to convert it into electrical signals, which correspond to the intensity of the detected light;

a gas inlet, which is designed to exchange gases and gas mixtures with the measurement environment by means of diffusion;

an optical filter element, which is arranged in front of the measuring detector and is designed as an optical band path filter to transmit light in the infrared optical range, preferably in a wavelength range of 3,200 nm to 3,500 mm;

an optical filter element, which is arranged in front of the at least one reference detector and is designed as at least one optical band pass element to transmit light in the infrared optical range, preferably in a wavelength range of 3,000 nm to 3,200 nm, and is designed to transmit light in the infrared optical range, preferably in a wavelength range of 3,800 nm to 4,000 nm; and an operating and analyzing unit, which is designed to operate the radiation source and to detect the electrical signals of the measuring detector and of the at least one reference detector, and which is designed, furthermore, to compensate the effect of the atmospheric humidity from the signal belonging to the first reference wavelength $\lambda_{R1}$, from the signal belonging to the second reference wavelength $\lambda_{R2}$ and from the signal belonging to the measurement wavelength $\lambda_M$, including the spectral measuring sensitivity characteristic of the measuring detector and the spectral measuring sensitivity characteristic of the at least one reference detector, preferably including the spectral emission characteristic of the radiation source, more preferably including the spectral transmission properties of the first optical filter element and the spectral transmission properties of the at least one second optical filter element, and to determine a target gas concentration, wherein the radiation source, the measuring detector and the at least one reference detector are arranged in the measuring cuvette and wherein the measuring cuvette is provided as a multireflection measuring cuvette with optically reflecting surfaces on the inner walls and wherein the light emitted from the radiation source reaches the measuring detector and the at least one reference detector after an at least single-time reflection on the reflecting surfaces of the measuring cuvette.

The measurement wavelength in the range of 3,200 nm to 3,500 nm is selected to be such that absorption by the target gas represented by a hydrocarbon compound, especially methane or propane, is guaranteed at the effective optical path length in the multireflection measuring cuvette.

The first reference wavelength in the range of 3,000 nm to 3,200 nm and the second reference wavelength in the range of 3,800 nm to 4,000 nm are selected to be such that there is no absorption by the target gas represented by a hydrocarbon compound, especially methane or propane, or by another gas of the measurement environment at the effective optical path length in the multireflection cuvette.

Heating elements, which are designed to temper the measuring detector and/or the at least one reference detector and/or the walls of the measuring cuvette, are arranged in the measurement arrangement in an optional and preferred manner. The heating elements are also preferably designed to temper the measuring detector and/or the at least one reference detector and/or the walls of the measuring cuvette in a temperature range of 5° C. to 15° C. above the ambient temperature. The heating elements are also preferably arranged on the rear side of or in the vicinity of the measuring detector and/or preferably on the rear side or in the vicinity of the at least one reference detector, as well as on the rear side of the walls or at the walls of the measuring cuvette.

In an optional variant of the measurement arrangement, the radiation source, the measuring detector and the at least one reference detector are arranged on the same side, preferably on one of the front sides, of the measuring cuvette, and also preferably essentially next to each other, in the measuring cuvette.

Further components of the measurement arrangement for the infrared optical measurement of gases and gas mixtures are a driving unit, which is designed to operate the heating elements, an energy supply unit, which is designed to supply the radiation source, the heating elements, the operating and analyzing unit and the driving unit with electric energy and preferably also designed to be supplied with electric energy from the outside via a feed interface, as well as an outer housing, which encloses the components and which is designed to receive the elements of the measurement arrangement, such as the measuring cuvette with the radiation source, gas inlet, protective element, measuring detector and at least one reference detector and/or preferably the operating and analyzing unit, as well as the other components, such as the driving unit and energy supply unit.

The measurement wavelength filter element and/or the at least one reference wavelength filter element are preferably designed as an optical interference filter.

The measurement wavelength filter element and/or the at least one reference wavelength filter element are preferably designed as a diffractive optical element.

The measurement wavelength filter element and/or the at least one reference wavelength filter element are preferably designed as an optical interference filter or as a diffractive optical element.

A protective element, which is designed to prevent the passage of contaminants from the measurement environment into the measuring cuvette, is preferably arranged at the gas inlet towards the measurement environment.

A display unit, which is designed to display measured values, disturbances and states of alarm, is also preferably arranged in the housing. The exceeding of a lower explosion unit (LEL) is an example of a typical state of alarm.

A communication unit, which is designed to transmit measured values, disturbances and states of alarm to a center via a data interface, is arranged in the housing in another optional manner.

Alarm units, which are designed to optically or acoustically display disturbances and states of alarm, are arranged in the housing in another optional manner.

The measurement arrangement is optionally designed in an explosion-proof design as a measurement arrangement for infrared optical measurement, where the protective element arranged towards the measurement environment is designed to prevent energy from being transmitted or a spark from passing over from the measuring cuvette into the measurement environment. In this optional explosion-proof design of the measurement arrangement, the housing is designed such as to prevent energy from being transmitted or sparks from passing over from the housing with the components contained therein, namely, the measuring cuvette, radiation source, gas inlet, protective element, measuring detector and at least one reference detector, operating and analyzing unit and energy supply unit into the measurement environment.

At least one temperature sensor, which is designed to detect a temperature representing the measuring detector and the at least one reference detector and to pass it on as a signal to the driving unit, is optionally arranged at the walls of the measuring cuvette and/or in the vicinity of or at the measuring detector and the at least one reference detector and/or at the heating element, wherein the driving unit is designed and able to use the temperature signals to set, maintain, control or regulate the temperature of the heating elements and/or of the walls of the measuring cuvette and/or of the measuring detector and of the at least one reference detector in a preset temperature range or to a preset temperature value.

An optical element, which is designed to focus the light of the radiation source and to filter it spectrally in the wavelength range to a preferred range in the range of the infrared wavelength range, is arranged in front of the radiation source in a likewise optional manner.

The measurement arrangement is preferably designed according to the present invention as a structural unit. Such a structural unit comprises at least the measuring cuvette with the measuring detector, with the at least one reference detector, with the radiation source, with the optical elements arranged in front of the measuring detector and the at least one reference detector and the optical elements preferably arranged in front of the radiation source, and of the operating and analyzing unit.

However, the present invention also covers the case in which the operating and analyzing unit is designed such that it is fully or at least partly separated structurally from the other elements of the measurement arrangement.

In a structurally fully separated embodiment, the operating and analyzing unit with the means for operation and signal detection, signal processing, signal analysis, as well as with the means for calculating the target gas concentration from the signal belonging to the first reference wavelength $\lambda_{R1}$, from the signal belonging to the second reference wavelength $\lambda_{R2}$ and from the signal belonging to the measurement wavelength $\lambda_M$, with compensation of the effect of the atmospheric humidity, and preferably with output and/or display of the target gas concentration is arranged in a separate structural unit separated from the other elements of the measurement arrangement.

An at least partially structurally separated embodiment may contain the operation of the radiation source, of the measuring detector and of the at least one reference detector, as well as at least a first stage of signal detection and/or signal processing of the signals of the signal detector and of the at least one reference detector, preferably with data on special properties and features of the radiation source, of the measuring detector and of the at least one reference detector, and further preferable properties of the optical filter elements arranged in front of the measuring detector and the at least one reference detector in a first structural unit, while further stages of the signal detection, signal processing, signal filtering and signal analysis, as well as the final calculation of the target gas concentration from the signal belonging to the first reference wavelength $\lambda_{R1}$, from the signal belonging to the second reference wavelength $\lambda_2$ and from the signal belonging to the measurement wavelength $\lambda_M$, with compensation of the atmospheric humidity, as well as preferably an outputting and/or display of the target gas concentration are performed in a second structural unit.

The compensation of the environmental effect, especially of the effect of moisture, is carried out in a first embodiment according to the present invention by means of the analysis of the signal of the measuring detector and of the signals of a first reference detector in the operating and analyzing unit.

An optical measurement wavelength filter element, which transmits as a first band pass the light of the measurement wavelength $\lambda_M$ in the range of 3,200 nm to 3,500 nm to the measuring detector, is arranged in front of the measuring detector.

The typical bandwidth of the measurement wavelength filter element is in a range of +/−100 nm symmetrically with respect to the position of the measurement wavelength $\lambda_M$.

A tolerance range of the transmission of the measurement wavelength filter element is obtained, e.g., on the basis of manufacturing tolerances, as +/−50 nm in addition to the range in which the optical measurement wavelength filter element nominally transmits the light of the measurement wavelength $\lambda_M$ according to specification.

The measurement wavelength $\lambda_M$ is selected and coordinated for the specific absorption in the form of a signal reduction of the measured signal at the measuring detector by a preset target gas at a preset concentration over an effective optical path length in the measuring cuvette.

The effective optical path length is obtained in the form of the length of the measuring cuvette from the space available for constructing the measurement arrangement, as well as from the design embodiment of the measuring cuvette and the reflection properties of the walls of the multireflection measuring cuvette.

In an application with methane as the target gas, a specifically coordinated measurement wavelength $\lambda_M$, in the range of 3,200 nm to 3,500 nm leads to an exemplary, absorption-related signal reduction of the measured signal by 10% to 15% at the measuring detector by the target gas methane in a technical embodiment with a multireflection cuvette. As an example, an effective optical path length in the range of 12 cm to 17 cm is obtained in the measuring cuvette in this application with methane as the target gas. Furthermore, the specific absorption equals 10% to 15% of the measured signal at the measuring detection in this exemplary application with methane as the target gas at a preset methane concentration of 5 vol. %. A methane concentration of 5 vol. % approximately corresponds to a value of 100% of the lower explosion limit (LEL).

A specifically coordinated measurement wavelength $\lambda_M$, in the range of 3,300 nm to 3,500 nm is obtained in an application with propane as the target gas.

A first optical reference wavelength filter element, which is designed as a double band pass filter and transmits the light of the first reference wavelength $\lambda_{R1}$ in the range of 3,000 nm to 3,200 nm and the light of the second reference wavelength $\lambda_{R2}$ in the range of 3,800 nm to 4,000 nm to the first reference detector, is arranged in front of the first reference detector.

The light of the first reference wavelength $\lambda_{R1}$ and the light of the second reference wavelength $\lambda_{R2}$ are both transmitted through the double band pass filter and summarily reach the first reference detector as a common reference light quantity with essentially two spectral components $\lambda_{R1}+\lambda_{R2}$. This reference light quantity is detected as a zero signal by the first reference detector.

The typical bandwidths of the first reference wavelength filter element are in a range of +/−100 nm symmetrically with respect to the position of the reference wavelengths $\lambda_{R1}, \lambda_{R2}$.

The tolerance range of the reference wavelength filter element, e.g., based on manufacturing tolerances, is obtained as +/−50 nm in addition to the range in which the first optical reference wavelength filter element nominally transmits the light of the first reference wavelength $\lambda_{R1}$ and the light of the second reference wavelength $\lambda_{R2}$ according to specification.

The bandwidth of the wavelength filter elements is defined in the sense of the present invention as the range of the filter elements at which the transmission of the light through the filter element is reduced by not less than 3 dB in relation to the transmission of the light at the transmission wavelength, the transmission wavelength being defined as the measurement wavelength $\lambda_M$, and the first and second reference wavelengths $\lambda_{R1}, \lambda_{R2}$.

The measurement wavelength filter element and/or the first reference wavelength filter element are designed as a diffractive optical element in one variant of the first embodiment.

The measurement wavelength filter element and/or the first reference wavelength filter element are designed as an optical interference filter in another variant of the first embodiment.

Environmental effects, such as temperature, air pressure, salt content and especially the moisture content in the ambient air in the present invention, act both at the measurement wavelength $\lambda_M$, and at the first reference wavelength $\lambda_{R1}$ and at the second reference wavelengths $\lambda_{R2}$.

The first and second reference wavelengths $\lambda_{R1}, \lambda_{R2}$ are selected, on the one hand, as was described above, such that there are no signal reductions due to the target gas or due to another gas from the measurement environment. Furthermore, the first and second reference wavelengths $\lambda_{R1}, \lambda_{R2}$ are selected to be such that environmental effects, especially the direct effect of atmospheric humidity and the indirect effect of atmospheric humidity caused by the salt content, will arise summarily as the same effect manifested as a signal reduction, which corresponds to the effect manifested as a signal reduction at the measurement wavelength $\lambda_M$.

The first reference wavelength $\lambda_{R1}$ is selected for this in a first variant of this first embodiment such that the effect of the atmospheric humidity is less marked than at the measurement wavelength $\lambda_M$ and the second reference wavelength $\lambda_{R2}$ is selected such that the effect of the atmospheric humidity is more pronounced than at the measurement wavelength $\lambda_M$.

The first reference wavelength $\lambda_{R1}$ is selected in a second variant of this first embodiment such that the effect of the atmospheric humidity is more pronounced than at the measurement wavelength $\lambda_M$ and the second reference wavelength $\lambda_{R2}$ is selected such that the effect of the atmospheric humidity is less marked than at the measurement wavelength $\lambda_M$.

An effect that is summarily on the order of magnitude that corresponds essentially to the effect of the atmospheric humidity at the measurement wavelength $\lambda_M$ is obtained in the first and second variants of this first embodiment at the first reference detector from the weaker and stronger effects of the direct and indirect effect of the atmospheric humidity on the reference wavelengths $\lambda_{R1}$, $\lambda_{R2}$ relative to the effect at the measurement wavelength $\lambda_M$. A summary zero signal, which can be used for the measured signal as a reference variable for determining the gas concentration, is also available with this summary effect under the effect of moisture in the operating and analyzing unit. The gas concentration of the target gas is determined in the operating and analyzing unit by referring and relating the measured signal to the zero signal. The moisture effect on the gas concentration determined in the operating and analyzing unit is eliminated in this manner, because it affects both the measured signal corresponding to the measurement wavelength $\lambda_M$ and the summary zero signal, which summarily corresponds to the first and second reference wavelengths, in the same direction.

The compensation of the environmental effect, especially of the effect of moisture is carried out in a second embodiment according to the present invention by means of the analysis of the signals of the measuring detector and of the signals of a first reference detector and of the signals of a second reference detector in the operating and analyzing unit. Unlike in the first embodiment, two reference detectors with a corresponding reference wavelength filter element each are used in the second embodiment.

The two reference detectors are called a first reference detector and a second reference detector in the second embodiment.

The two corresponding reference wavelength filter elements are called a first reference wavelength filter element and a second reference wavelength filter element in the second embodiment.

An optical measurement wavelength filter element, which transmits as a first band pass the light of the measurement wavelength $\lambda_M$ in the range of 3,200 nm to 3,500 nm to the measuring detector, is arranged in front of the measuring detector.

The typical bandwidth of the measurement wavelength filter element is in a range of +/−100 nm symmetrically with respect to the position of the measurement wavelength $\lambda_M$.

A tolerance range of the measurement wavelength filter element, e.g., on the basis of manufacturing tolerances, is obtained with +/−50 nm in addition to the range in which the optical measurement wavelength filter element nominally transmits the light of the measurement wavelength $\lambda_M$ according to specification.

As in the first embodiment, the measurement wavelength $\lambda_M$ is selected and coordinated specifically for the specific absorption in the form of a signal reduction of the measured signal at the measuring detector due to a preset target gas at a preset concentration over an effective optical path length in the measuring cuvette.

The effective optical path length is obtained in the form of the length of the measuring cuvette from the space available for constructing the measurement arrangement as well as from the design embodiment of the measuring cuvette and the reflection properties of the walls of the multireflection measuring cuvette.

In an application with methane as the target gas, a specifically coordinated measurement wavelength $\lambda_M$ in the range of 3,200 n, to 3,500 nm in a technical embodiment with a multireflection cuvette leads to an exemplary, absorption-related signal reduction by 10% to 15% of the measured signal at the measuring detector by the target gas methane. An effective optical path length in the measuring cuvette in the range of 12 cm to 17 cm is obtained in this application with methane as the target gas in case of an overall inner length of 5 cm of the measuring cuvette. Furthermore, the specific absorption of 10% to 15% of the measured signal is obtained at the measuring detector in this exemplary application with methane as the target gas at a preset methane concentration of 5 vol. %. A methane concentration of 5 vol. % approximately corresponds to a value of 100% of the lower explosion limit (LEL).

A specifically coordinated measurement wavelength $\lambda_M$, in the range of 3,300 nm to 3,500 nm is obtained in an application with propane as the target gas.

A first optical reference wavelength filter element, which as a band pass filter transmits the light of the first reference wavelength $\lambda_{R1}$ in the range of 3,000 nm to 3,200 nm to the first reference detector, is arranged in front of the first reference detector.

A second optical reference wavelength filter element, which as a band pass filter transmits the light of the second reference wavelength $\lambda_{R2}$ in the range of 3,800 nm to 4,000 nm to the second reference detector, is arranged in front of the second reference detector.

The light of the first reference wavelength $\lambda_{R1}$ is transmitted by the first optical reference wavelength filter element and reaches the first reference detector as a first component of a reference light quantity essentially with the spectral component $\lambda_{R1}$.

The light of the second reference wavelength $\lambda_{R2}$ is transmitted by the second optical reference wavelength filter element and reaches the second reference detector as a second component of the reference light quantity essentially with the spectral component $\lambda_{R2}$.

The first and second components of the reference light quantity are combined into a zero signal after the detection by the first and second reference detectors in the operating and analyzing unit.

The typical bandwidth of the first reference wavelength filter element is in a range of +/−100 nm symmetrically with respect to the position of the first reference wave wavelength $\lambda_{R1}$.

The typical bandwidth of the second reference wavelength filter element is in a range of +/−100 nm symmetrically with respect to the position of the second reference wave wavelength $\lambda_{R2}$.

A tolerance range of the transmission of the first and second reference wavelength filter elements, e.g., based on manufacturing tolerances, is obtained with +/−50 nm in addition to the range in which the first optical reference wavelength filter element nominally transmits the light of the first reference wavelength $\lambda_{R1}$ according to specification and the second reference wavelength filter element nominally transmits the light of the second reference wavelength $\lambda_{R2}$ according to specification.

In one variant of the second embodiment, the measurement wavelength filter element and/or the first reference wavelength filter element and/or the second reference wavelength filter element are designed as a diffractive optical element.

In another variant of the second embodiment, the measurement wavelength filter element and/or the first reference wavelength filter element and/or the second reference wavelength filter element are designed as an optical interference filter.

Environmental effects, such as temperature, air pressure, salt content and, in the present invention especially the moisture of the atmospheric air, act both at the measurement wavelength $\lambda_M$ and at the first reference wavelength $\lambda_{R1}$ and at the second reference wavelength $\lambda_{R2}$.

As was described above, the first and second reference wavelengths $\lambda_{R1}$, $\lambda_{R2}$ are selected, on the one hand, such that there will be no signal reductions due to the target gas or due to other gases of the measurement environment. Furthermore, the first and second reference wavelengths $\lambda_{R1}$, $\lambda_{R2}$ are selected to be such that environmental effects, especially the direct effect of atmospheric humidity as well as the indirect effect of the atmospheric humidity due to the salt content, lead, in combination in the zero signal determined in the operating and analyzing unit, to the same effect as a signal reduction, which corresponds to the effect manifested as signal reduction at the measurement wavelength $\lambda_M$.

The first reference wavelength $\lambda_{R1}$ is selected for this in a first variant of this second embodiment such that the direct and indirect effects of the atmospheric humidity are less marked than at the measurement wavelength $\lambda_M$, and the second reference wavelength $\lambda_{R2}$ is selected such that the direct and indirect effects of the atmospheric humidity are more pronounced than at the measurement wavelength $\lambda_M$.

In a second variant of this second embodiment, the first reference wavelength $\lambda_{R1}$ is selected to be such that the direct and indirect effects of the atmospheric humidity are more pronounced than at the measurement wavelength $\lambda_M$ and the second reference wavelength $\lambda_{R2}$ is selected to be such that the direct and indirect effects of the atmospheric humidity are less marked than at the measurement wavelength $\lambda_M$. An effect, which corresponds to the effect of the atmospheric humidity at the measurement wavelength $\lambda_M$ at the measuring detector, is obtained in both variants of this second embodiment from the weaker and stronger effect of the direct and indirect effects of the atmospheric humidity on the signal corresponding to the first reference wavelength $\lambda_{R1}$ at the first reference detector and on the signal corresponding to the second reference wavelength $\lambda_{R2}$ at the second reference detector in the operating and analyzing unit. Thus, a zero signal, which is suitable for the measured signal as a reference variable for determining the gas concentration, is available under the effect of moisture in the operating and analyzing unit in this second embodiment as well.

The gas concentration of the target gas is determined in the operating and analyzing unit, just as in the first embodiment, by referring and relating the measured signal at the measuring detector to the zero signal.

The moisture effect on the gas concentration determined in the operating and analyzing unit is eliminated in this manner, because it acts in the same direction on both the measured signal corresponding to the measurement wavelength $\lambda_M$ and the zero signal, which was determined on the basis of the signal of the first and second reference wavelengths at the first and second reference detectors.

The first and second reference wavelengths $\lambda_{R1}$ and $\lambda_{R2}$ are selected in relation to the measurement wavelength $\lambda_M$ in a preferred variant of the first and second embodiments such that the spectra emission characteristic of the radiation source is taken into account.

The spectral emission characteristic of the radiation is taken into account by selecting the first reference wavelength $\lambda_{R1}$ such that the absorption caused by the moisture effect at the first reference wavelength $\lambda_{R1}$ and the spectral light intensity caused by the spectral emission characteristic of the radiation source at the first reference wavelength $\lambda_{R1}$ summarily yield a first component of the zero signal, which yields, summarily with the second component of the zero signal, which is obtained summarily from the absorption caused by the moisture effect at the second reference wavelength $\lambda_{R2}$ and the spectral light intensity caused by the spectral emission characteristic of the radiation source at the second reference wavelength $\lambda_{R2}$, the zero signal, which corresponds to the effect of the absorption caused by the moisture at the measurement wavelength $\lambda_M$ and to the spectral light intensity caused by the spectral emission characteristic of the radiation source at the measurement wavelength $\lambda_M$.

The first and second reference wavelengths $\lambda_{R1}$ and $\lambda_{R2}$ are selected in another preferred variant of the first and second embodiments such that the transmission properties of the at least one reference wavelength filter element and of the measurement wavelength filter element are also taken into account.

The transmission properties are taken into account by selecting the first reference wavelength $\lambda_{R1}$ to be such that the first component of the zero signal is obtained summarily from the absorption caused by the moisture effect at the first reference wavelength $\lambda_{R1}$ and the transmission properties of the at least one reference wavelength filter element at the first reference wavelength $\lambda_{R1}$ and the second component of the zero signal is summarily obtained from the absorption caused by the moisture effect at the second reference wavelength $\lambda_{R2}$ and the transmission properties of the at least one reference wavelength filter element at the second reference wavelength $\lambda_{R2}$, so that the zero signal corresponds to the effect of the absorption caused by the moisture effect at the measurement wavelength $\lambda_M$ and the transmission properties of the measurement wavelength filter element at the measurement wavelength $\lambda_M$.

In another preferred variant of the first and second embodiments, the first and second reference wavelengths $\lambda_{R1}$ and $\lambda_{R2}$ are selected in relation to the measurement wavelength $\lambda_M$ such that the spectral emission characteristic of the radiation source and the transmission properties of the measurement wavelength filter element and of the at least one reference wavelength filter element are taken into account.

The spectral emission characteristic and the transmission properties are taken into account by selecting the first reference wavelength $\lambda_{R1}$ such that the first component of the zero signal is obtained summarily from the absorption caused by the moisture effect at the first reference wavelength $\lambda_{R1}$ and the transmission properties of the at least one reference wavelength filter element and the spectral light intensity caused by the spectral emission characteristic of the radiation source at the first reference wavelength $\lambda_{R1}$ and the second component of the zero signal is obtained summarily from the absorption caused by the moisture effect at the second reference wavelength $\lambda_{R2}$ and the transmission properties of the at least one reference wavelength filter element and the spectral light intensity caused by the spectral emission characteristic of the radiation source at the second reference wavelength $\lambda_{R2}$, so that the zero signal corresponds to the effect of the absorption caused by the moisture effect at the measurement wavelength $\lambda_M$ and the transmission properties of the measurement wavelength filter element and the spectral light intensity caused by the spectral emission characteristic of the radiation source at the measurement wavelength $\lambda_M$.

In another preferred embodiment, which can be combined with the three above-described embodiments each, not only is the position of the first and second reference wavelengths selected in relation to the measurement wavelength $\lambda_M$ in the spectral range as a function of the emission characteristic of the radiation source, the transmission properties of the at least one reference wavelength filter element and of the measurement wavelength filter element, and the absorption caused by the moisture effect at the first and second reference wavelengths, but the transmission properties of the at least one reference wavelength filter element are also adapted, moreover, to the emission characteristics of the radiation source and/or to the measuring sensitivity of the at least one reference detector at the first and second reference wavelengths.

The bandwidth of the at least one reference wavelength filter element is selected for this for the first and second reference wavelengths such that they are different and also differ from each other, so that the curve describing the spectral intensity of the radiation source and/or the different measuring sensitivities of the at least one reference detector at the first and second reference wavelengths are also taken into account and compensated.

The four preferred variants of the first and second embodiments described make it possible to select the reference wavelengths $\lambda_{R1}$, $\lambda_{R2}$ on the spectral scale above and below the measurement wavelength $\lambda_M$, and the exact position of the reference wavelengths $\lambda_{R1}$, $\lambda_{R2}$ on the spectral scale is determined in relation to the measurement wavelength $\lambda_M$, not only by environmental effects, especially the moisture effect, but the exact selection of the reference wavelengths $\lambda_{R1}$, $\lambda_{R2}$ on the spectral scale is also determined by the further components of the measurement arrangement.

In a simplified first approach for determining the reference wavelengths $\lambda_{R1}$, $\lambda_{R2}$ according to the first embodiment with a double band pass as a reference wavelength filter element, in which the transmission properties of the measurement wavelength filter element and of the reference filter element, as well as the spectral emission characteristic of the radiation source are not taken into account, and under the assumption that the light absorption caused by the moisture effect is described essentially by a curve that can be described by a linearly dropping function over the optical measurement section in the spectral range below the measurement wavelength $\lambda_M$, and in the range above the measurement wavelength $\lambda_M$, an essentially symmetrical distance of the two reference wavelengths $\lambda_{R1}$, $\lambda_{R2}$ from the measurement wavelength $\lambda_M$ is obtained. For example, a first reference wavelength $\lambda_{R1}$ of 3,100 nm and a second reference wavelength $\lambda_2$ of 3,900 nm are thus obtained at a measurement wavelength $\lambda_M$ of 3,300 nm according to the simplified approach.

Taking a variable course of the spectral intensity of the radiation source in the wavelength range of the first and second reference wavelengths $\lambda_{R1}$, $\lambda_{R2}$ and of the measurement wavelength $\lambda_M$, into account, taking into account a light absorption caused by the deviation from the linear course due to the moisture effect over the optical measurement section in the spectral range above and below the measurement wavelength $\lambda_M$, into account, and taking into account the spectral emission characteristic of the radiation source and the transmission properties of the measurement wavelength filter element and the transmission properties of the reference wavelength filter element, a design with a first reference wavelength $\lambda_{R1}$ of 3,100 nm and with a second reference wavelength $\lambda_{R2}$ of 3,900 nm is obtained in a second approach according to the first embodiment with a reference wavelength filter element designed as a double band pass at a measurement wavelength $\lambda_M$ of 3,300 nm.

The formation of the zero signal and the moisture compensation based on it will be explained in more detail in a simplified form by means of the following formulas. In the sense of a simplified representation, the absorption is described in the manner of an absorption signal, which is defined both as a physical variable and an electrical variable.

Symbols:
$\lambda_M$: Measurement wavelength
$\lambda_{R1}$: fist reference wavelength $\lambda_{R1}$
$\lambda_{R2}$: Second reference wavelength $\lambda_{R2}$
$A(\lambda)$: Absorption signal as a function of a wavelength $\lambda$
Z: Target gas
K(Z): Target gas concentration
H: Relative atmospheric humidity in the gas chamber of the measuring cuvette
$T(\lambda)$: Transmission properties of the wavelength filter element at wavelength $\lambda$
$SR(\lambda)$: Emission properties of the radiation source at wavelength $\lambda$
$A(\lambda_{R1}, \lambda_{R2})$: Summary reference absorption signal at the first reference wavelength $\lambda_{R1}$ and at the second reference wavelength $\lambda_{R2}$
$A(H, \lambda_{R1})$: Absorption signal caused by the atmospheric humidity, at the reference wavelength $\lambda_{R1}$
$A(H, \lambda_M)$: Absorption signal caused by the atmospheric humidity at the second reference wavelength $\lambda_{R2}$
$A(H, \lambda_M)$: Absorption signal caused by the atmospheric humidity at the measurement wavelength $\lambda_M$
$A(Z, \lambda_{R1})$: Absorption signal caused by the target gas at the first reference wavelength $\lambda_{R1}$
$A(Z, \lambda_{R2})$: Absorption signal caused by the target gas at the second reference wavelength $\lambda_{R2}$
$A(Z, \lambda_M)$: Absorption signal caused by the target gas at the measurement wavelength $\lambda_M$
$A(0, \lambda_M)$: Zero signal, without absorption by the target gas and without moisture effect at the measurement wavelength $\lambda_M$
$A(0, H, \lambda_M)$: Zero signal, without absorption by the target gas and with moisture effect at the measurement wavelength $\lambda_M$
$A(Z, H, \lambda_{R1}, \lambda_{R2})$: Summary absorption signal at the first reference wavelength $\lambda_{R1}$ and at the second reference wavelength $\lambda_{R2}$ caused by the atmospheric humidity and by the target gas
$A(Z, H, \lambda_M)$: Summary absorption signal at the measurement wavelength $\lambda_M$, caused by the atmospheric humidity and by the target gas
$A(Z, H, T, S, \lambda_{R10}, \lambda_{R20})$: Summary absorption signal at the adapted reference wavelengths $\lambda_{R10}$ and $\lambda_{R20}$ caused by the atmospheric humidity and caused by the target gas, including the transmission properties of the at least one reference wavelength filter element at the adapted reference wavelengths $\lambda_{R10}$, $\lambda_{R20}$ and of the emission properties of the radiation source at the adapted reference wavelengths $\lambda_{R10}$, $\lambda_{R20}$
$A(Z, H, T, S, \lambda_M)$: Summary absorption signal at the measurement wavelength $\lambda_M$, caused by the atmospheric humidity and caused by the target gas, including the transmission properties of the measurement wavelength filter element at the measurement wavelength $\lambda_M$, and of the emission properties of the radiation source at the measurement wavelength $\lambda_M$.

The following explanations and derivations describe the compensation of the moisture effect on the basis of the simplified equations.

The reference wavelengths are selected such that there is no absorption by the target gas at the first and second reference wavelengths $\lambda_{R1}$, $\lambda_{R2}$. This is described by Formula [1] and Formula [2].

$$A(Z, \lambda_{R1}) = 0 \quad [1]$$

$$A(Z, \lambda_{R2}) = 0 \quad [2]$$

Absorption takes place with an effect of a signal reduction by k1 due to the target gas without moisture effect at the measurement wavelength $\lambda_M$.

The measurement wavelength $\lambda_M$ and the effective optical path length are coordinated with one another and selected such that a signal reduction by k1=0.85 will occur relative to the zero signal $A(0, \lambda_M)$ for the target gas methane. This is described by Formula [3].

$$A(Z, \lambda_M) = k1 * A(0, \lambda_M) \quad [3]$$

There is an additional signal reduction by k2 relative to the zero signal $A(0, \lambda_M)$ and relative to the measured signal $A(Z, \lambda_M)$ in the presence of the target gas due to the moisture effect at the measurement wavelength $\lambda_M$. This is described by Formula [4].

$$A(Z, H, \lambda_M) = k2 * k1 * A(0, \lambda_M) \quad [4]$$

The absorption at the reference moisture is obtained summarily as a reference absorption signal from the absorption caused by the atmospheric humidity and by the target gas. This is described by Formula [5].

$$A(Z, H, \lambda_{R1}, \lambda_{R2}) = A(Z, \lambda_{R1}) + A(Z, \lambda_{R2}) + A(H, \lambda_{R1}) + A(H, \lambda_{R2}) \quad [5]$$

Taking [1] and [2] into account, Formula [5] becomes simplified to Formula [6].

$$A(H, \lambda_{R1}, \lambda_{R2}) = A(H, \lambda_{R1}) + A(H, \lambda_{R2}) \quad [6]$$

Including the signal reduction k2, Formula [7] is obtained from this as a summary reference absorption signal in relation to the absorption at the reference wavelengths without moisture effect.

$$A(H, \lambda_{R1}, \lambda_{R2}) = A(H, \lambda_{R1}) + A(H, \lambda_{R2}) = k2 * (A(\lambda_{R1}) + A(\lambda_{R2})) \quad [7]$$

If the measured signal $A(Z, H, \lambda_M)$ [4] is related to the summary reference signal $A(H, \lambda_{R1}, \lambda_{R2})$ [6], [7] as a quotient [8], the concentration signal is obtained as a function of the target gas with compensation for the moisture effect.

$$K(Z, H) = (k2 * k1 * A(0, \lambda_M))/(k2 * (A(\lambda_{R1}) + A(\lambda_{R2}))) \quad [8]$$

$$K(Z, H) = (k1 * A(0, \lambda_M))/(A(\lambda_{R1}) + A(\lambda_{R2})) \quad [9]$$

It can be seen from this that the moisture effect k2 can be eliminated in Formula [2] and the target gas concentration is thus obtained from the signal reduction k1 relative to the zero signal $A(0, \lambda_M)$ at the measurement wavelength $\lambda_M$ and the summary reference signal $A(\lambda_{R1}, \lambda_{R1})$ at the reference wavelengths $\lambda_{R1}, \lambda_{R2}$.

Taking the emission properties of the radiation source and the transmission properties of the filter elements into account, an expanded Formula [10] is obtained for the measurement wavelength and an expanded Formula [11] is obtained for reference wavelengths $\lambda_{R10}, \lambda_{R20}$ adapted to these emission properties of the radiation source and the transmission properties of the reference wavelength filter elements. The emission properties $S(\lambda_M)$ of the radiation source at the measurement wavelength $\lambda_M$ and the transmission properties of the measurement wavelength filter element at the measurement wavelength $\lambda_M$ are included in an adapted reduction factor k10.

The emission properties $S(\lambda_{R10}, \lambda_{R20})$ and transmission properties $T(\lambda_{R10}, \lambda_{R20})$ of the reference wavelength filter elements are included in an adapted factor k20 in addition to the moisture effect H. Besides the transmission at the wavelength, the respective bandwidths, namely, $$A(Z, H, T, S, \lambda_M) = k20 * k10 * A(0, \lambda_M) \quad [9]$$

$$A(H, T, S, \lambda_{R10}, \lambda_{R20}) = A(H, T, S, \lambda_{R10}) + A(H, T, S, \lambda_{R20}) = k20 * (A(\lambda_{R10}) + A(\lambda k_{20})) \quad [10]$$

are also contained in the transmission properties of the measurement wavelength filter elements and the reference wavelength filter elements, so that a concentration signal is obtained in the quotient formation [11] as a function of the target gas with compensation of the moisture effect, taking the emission properties of the radiation source and the transmission properties of the reference wavelength filter elements with reference wavelengths $\lambda_{R10}, \lambda_{R20}$ adapted thereto into account.

$$K(Z, H, T, S) = (k20 * k10 * A(0, \lambda_M))/(k2 * (A(\lambda_{R10}) + A(\lambda_{R20}))) \quad [11]$$

$$K(Z, H, T, S) = (k10 * A(0, \lambda_M))/(A(\lambda_{R1}) + A(\lambda_{R2})) \quad [12]$$

The target gas concentration is thus obtained from the signal reduction k10 relative to the zero signal $A(0, \lambda_M)$ at the measurement wavelength $\lambda_M$ and the summary reference signal $A(\lambda_{R10}, \lambda_{R10})$ at the adapted reference wavelengths $\lambda_{R10}, \lambda_{R20}$.

The present invention will be explained in more detail in its preferred embodiments on the basis of the following figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1b is a schematic detail view of the first embodiment of the measurement arrangement according to FIG. 1a;

FIG. 2b is a schematic detail view of the second embodiment of the measurement arrangement in accordance with FIG. 2a.

DESCRIPTION OF THE PREFERRED EMBODIMENTS

Figure 1A:
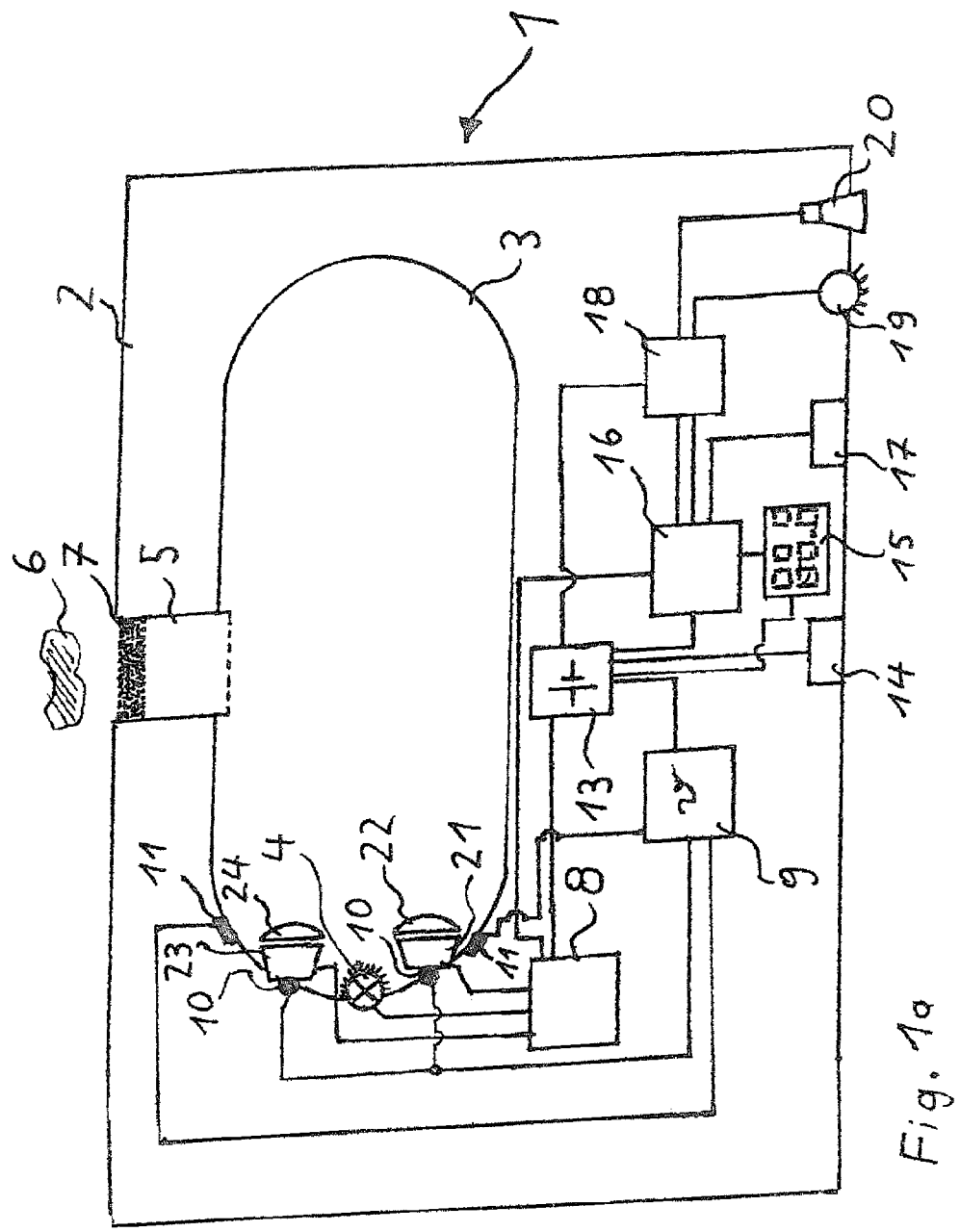
FIG. 1a is a schematic view of a first embodiment of a measurement arrangement for the infrared optical measurement of gases and gas mixtures, with compensation of environmental effects.
Figure 16:
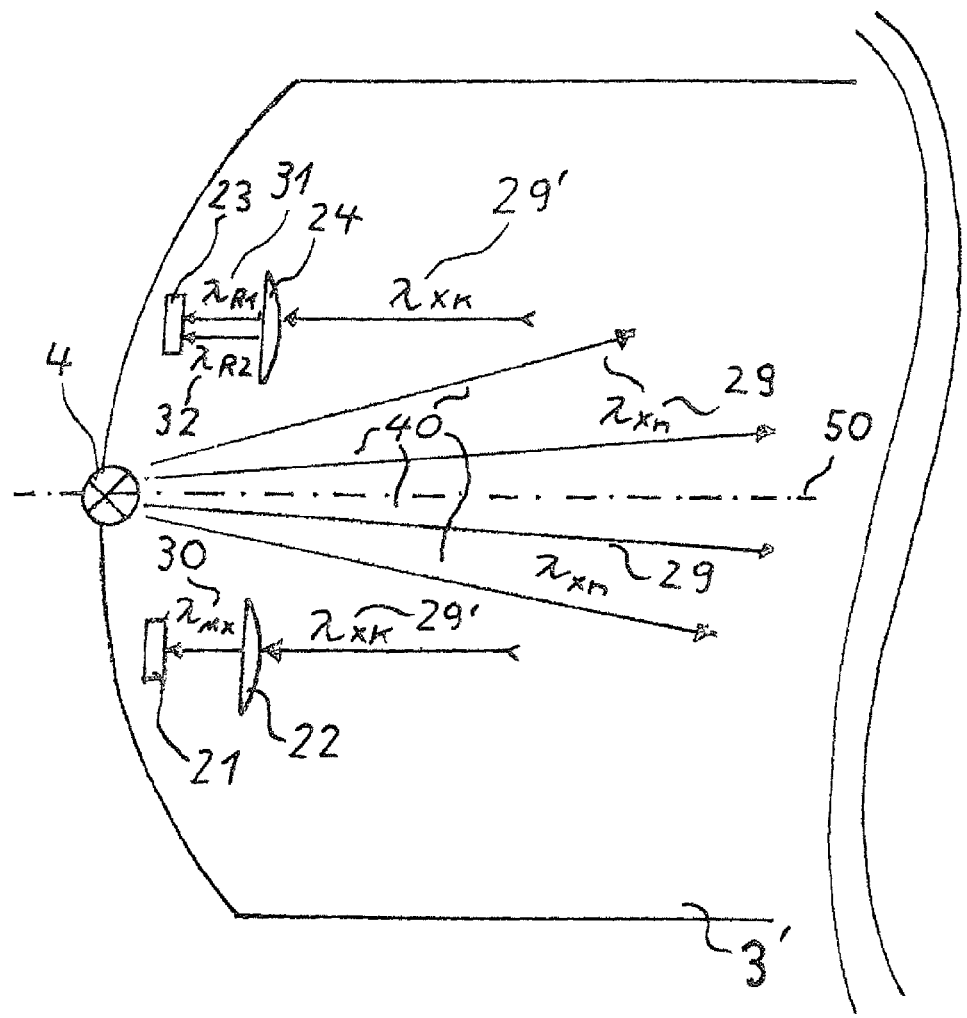

Referring to the drawings in particular, FIG. 1a shows a first measurement arrangement 1 for the infrared optical measurement of gases and gas mixtures, with compensation of environmental effects, with a housing 2 with a measuring cuvette 3, an operating and analyzing unit 8, a driving unit 9, an energy supply unit 13 with a feed interface 14 arranged thereon, a communication unit 16, to which a display unit 15, an alarm unit 18 and a data interface 17 are connected.

The operating and analyzing unit 8 is connected to the driving unit 9, the energy supply unit 13 and the communication unit 16. The energy supply unit 13 supplies the alarm unit 18, the display unit 15, the driving unit 9, the communication unit 16 and the driving unit 9 with electric energy.

An optical alarm generator 19 and an acoustic alarm generator 20 are connected to the alarm unit 18.

The measuring cuvette 3 comprises a radiation source 4, a gas inlet 5 with a protective element 7 arranged towards the measurement environment 6, heating elements 10, a first temperature sensor 11 and a second temperature sensor 12, a measuring detector 21, a measurement wavelength filter element 22, a first reference detector 23 and a first reference wavelength filter element 24. The first temperature sensor 11 and the second temperature sensor 12, the measuring detector 21, and the first reference detector 23 are connected to the operating and analyzing unit 8. The measuring cuvette 3 is designed as a multireflection measuring cuvette 3 in this first measurement arrangement 1.

The radiation source 4 emits light in an infrared wavelength range X (FIG. 1b) into the measuring cuvette 3, and this light is reflected multiple times in the measuring cuvette 3, absorbed by the target gas along the optical path length of the measuring cuvette 3, and reaches as IR light $\lambda_{Xk}$ 29' (FIG. 1b) the measurement wavelength filter element 22 and the first reference wavelength filter element 24.

The measurement wavelength filter element 22 transmits from the infrared wavelength range $\lambda_{Xk}$ 29' only a component of the light in the range of the IR wavelength $\lambda_{Mx}$ 30 (FIG. 1b) to the measuring detector 21.

The first reference wavelength filter element 24 transmits from the infrared wavelength range $\lambda_{Xk}$ 29' (FIG. 1b) only a component of the light in the range of the first IR reference wavelength $\lambda_{Rx1}$ 31 (FIG. 1b) and a component of the light in the range of the second IR reference wavelength $\lambda_{Rx2}$ (FIG. 1b) to the first reference detector 23. The signals of the measuring detector 21, corresponding to the intensity of the measurement wavelength $\lambda_{Mx}$ 30 (FIG. 1b) detected by the first measuring detector 21, and the signals of the first reference detector 23, corresponding to the summary intensity of the first reference wavelength $\lambda_{Rx1}$ 31 (FIG. 1b) detected by the first reference detector 23 and of the second reference wavelength $\lambda_{Rx1}$ 31 (FIG. 1b), are combined with one another in the operating and analyzing unit 8 in such a way that a target gas concentration is determined. This target gas concentration is sent by the operating and analyzing unit 8 to the communication unit 16, and from there to the display unit 15, alarm unit 18 and data interface 17. If certain limit values of the target gas concentration are exceeded, alarms are triggered by means of the alarm unit 18 via the optical alarm generator 19 and/or the acoustic alarm generator 20.

A piece 3' of the measuring cuvette 3 according to FIG. 1a is shown in FIG. 1b. Identical elements in FIG. 1a and FIG. 1b are designated by the same reference numbers as in FIG. 1a.

The piece 3' shown shows the metrological elements arranged on one side of the measuring cuvette 3 (FIG. 1a) (radiation source 4, measuring detector 21, measurement wavelength filter element 22, first reference detector 23, first reference wavelength filter element 24).

The radiation source 4 emits light as an essentially inhomogeneous light bundle 40 along an optical axis 50 in an infrared wavelength range $\lambda_{Xn}$ 29 into the measuring cuvette 3 (FIG. 1a); this light is reflected multiple times in the multireflection measuring cuvette 3 (FIG. 1a), absorbed by the target gas along the optical path length of the measuring cuvette 3 (FIG. 1a), and reaches as IR light $\lambda_{Xk}$ 29' the measurement wavelength filter element 22 and the first reference wavelength filter element 24.

The measurement wavelength filter element 22 transmits from the infrared wavelength range $\lambda_{Xk}$ 29' only a component of the light in the range of the IR measurement wavelength $\lambda_{Mx}$ 30 to the measuring detector 21.

The first reference wavelength filter element 24 transmits from the infrared wavelength range $\lambda_{Xk}$ 29' only a component of the light in the range of the first IR reference wavelength $\lambda_{Rx1}$ 31 and a component of light in the range of the second IR reference wavelength $\lambda_{Rx2}$ to the first reference detector 23.

The measuring detector 22 and the reference detector 23 are connected to the operating and analyzing unit 8 (FIG. 1a), so that the signals of the measuring detector 22 and of the reference detector 23 can be analyzed in the operating and analyzing unit 8 (FIG. 1a) in order to determine a target gas concentration with compensation of the effect of the moisture present in the target gas.

Figure 2A:
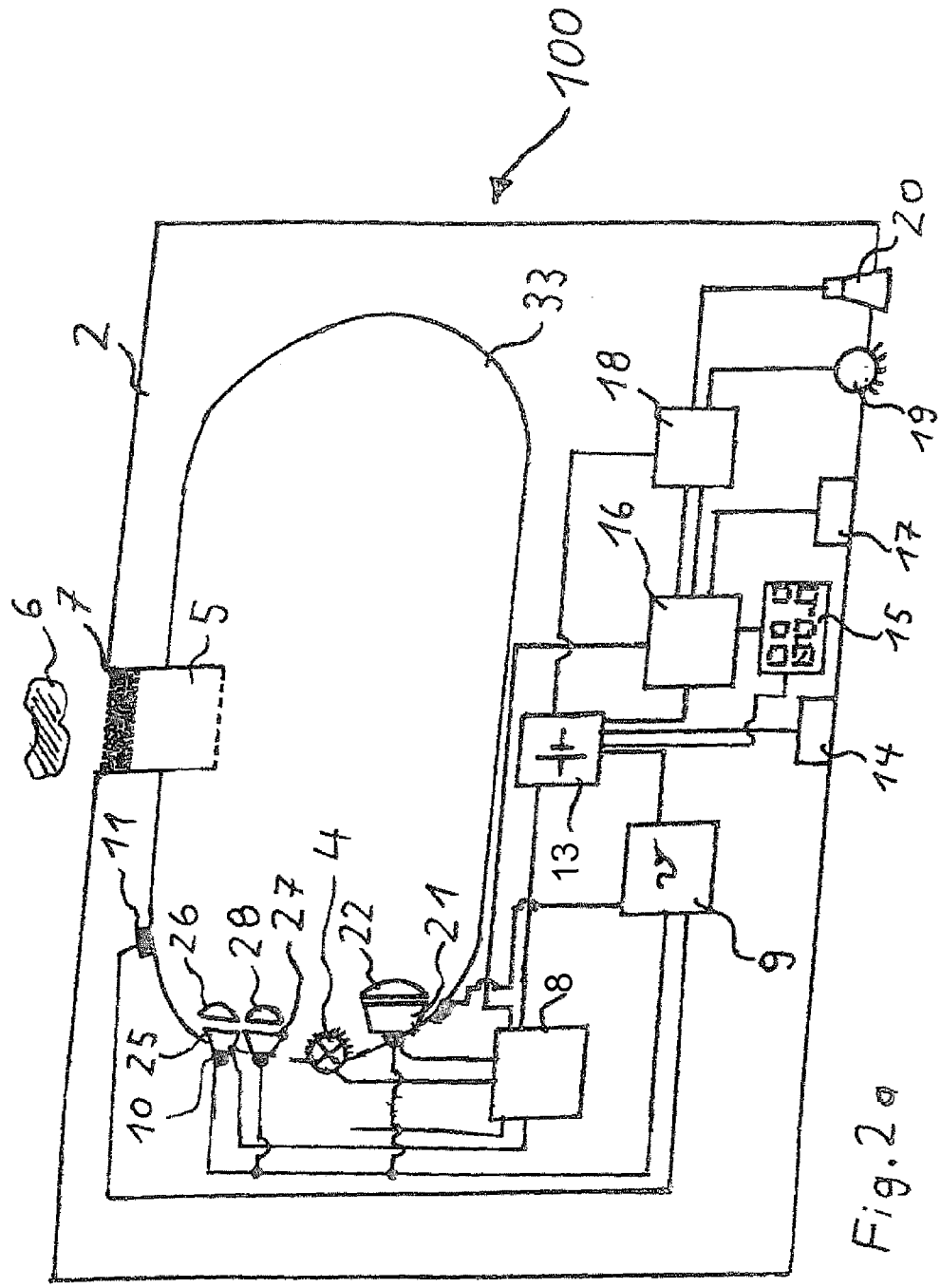
FIG. 2a is a schematic view of a second embodiment of a measurement arrangement for the infrared optical measurement of gases and gas mixtures, with compensation of environmental effects.

FIG. 2a shows a second measurement arrangement 100 for the infrared optical measurement of gases and gas mixtures with compensation of environmental effects. Identical components in FIG. 2a and in FIG. 1a are designated by the same reference numbers as in FIG. 1a.

The second measurement arrangement 100 is shown with a housing 2, with a measuring cuvette 33, with an operating and analyzing unit 8, with a driving unit 9, with an energy supply unit 13 with a feed interface 14 arranged thereon, and with a communication unit 16, to which a display unit 15, an alarm unit 18 and a data interface 17 are connected.

The operating and analyzing unit 8 is connected to the driving unit 9, the energy supply unit 13 and the communication unit 16. The energy supply unit 13 supplies the alarm unit 18, the display unit 15, the communication unit 16 and the driving unit 9 with electric energy.

An optical alarm generator 19 and an acoustic alarm generator 20 are connected to the alarm unit 18. The measuring cuvette 33 is designed as a multireflection measuring cuvette 3 in this second measurement arrangement 100.

The measuring cuvette 33 comprises a radiation source 4, a gas inlet 5 with a protective element 7 arranged towards the measurement environment 6, heating elements 10, a first temperature sensor 11 and a second temperature sensor 12, a measuring detector 21, a measurement wavelength filter element 22, a first reference detector 25, a first reference wavelength filter element 26, a second reference detector 27 and a second reference wavelength filter element 28. The first temperature sensor 21 as well as the first and second reference detectors 25, 27 are connected to the operating and analyzing unit 8.

The radiation source 4 emits light in an infrared wavelength range X into the measuring cuvette 3; this light is reflected multiple times in the measuring cuvette 3 (FIG. 1a), absorbed by the target gas along the optical path length of the measuring cuvette 3 (FIG. 1a) and reaches as IR light $\lambda_{Xk}$ 29' the measurement wavelength filter element 22, as well as the first reference wavelength filter element 26 and the second reference wavelength filter element 28. The measurement wavelength filter element 22 transmits from the infrared wavelength range $\lambda_{Xk}$ 29' (FIG. 2b) only a component of the light in the range of the IR measurement wavelength $\lambda_{Mx}$ 30 (FIG. 2b) to the measuring detector 21.

The first reference wavelength filter element 26 transmits from the infrared wavelength range $\lambda_{Xk}$ 29' (FIG. 2b) only a component of the light in the range of the first IR reference wavelength $\lambda_{Rx1}$ 31 (FIG. 2b) to the first reference detector 25.

The second reference wavelength filter element 28 transmits from the infrared wavelength range $\lambda_{Xk}$ 29' (FIG. 2b) only a component of the light in the range of the second IR reference wavelength $\lambda_{Rx2}$ 32 (FIG. 2b) to the second reference detector 27.

The signals of the measuring detector 21, corresponding to the intensity of the measurement wavelength $\lambda_{Mx}$ 30 (FIG. 2b) detected by the first measuring detector 21, and the signals of the first reference detector 25, corresponding to the intensity of the first reference wavelength $\lambda_{Rx1}$ 31 (FIG. 2b) detected by the first reference detector 25, and the signals of the second reference detector 27, corresponding to the intensity of the second reference wavelength $\lambda_{Rx2}$ 32 (FIG. 2b) detected by the second reference detector 27, are combined with one another in the operating and analyzing unit 8 in such a way that a target gas concentration is determined. This target gas concentration is sent by the operating and analyzing unit 8 to the communication unit 16, from there passed on to the display unit 15, alarm unit 18 and the data interface 17. If predetermined limit values of the target gas concentration are exceeded, alarms are triggered by means of the alarm unit 18 via the optical alarm generator 19 and/or the acoustic alarm generator 20.

Figure 2B:
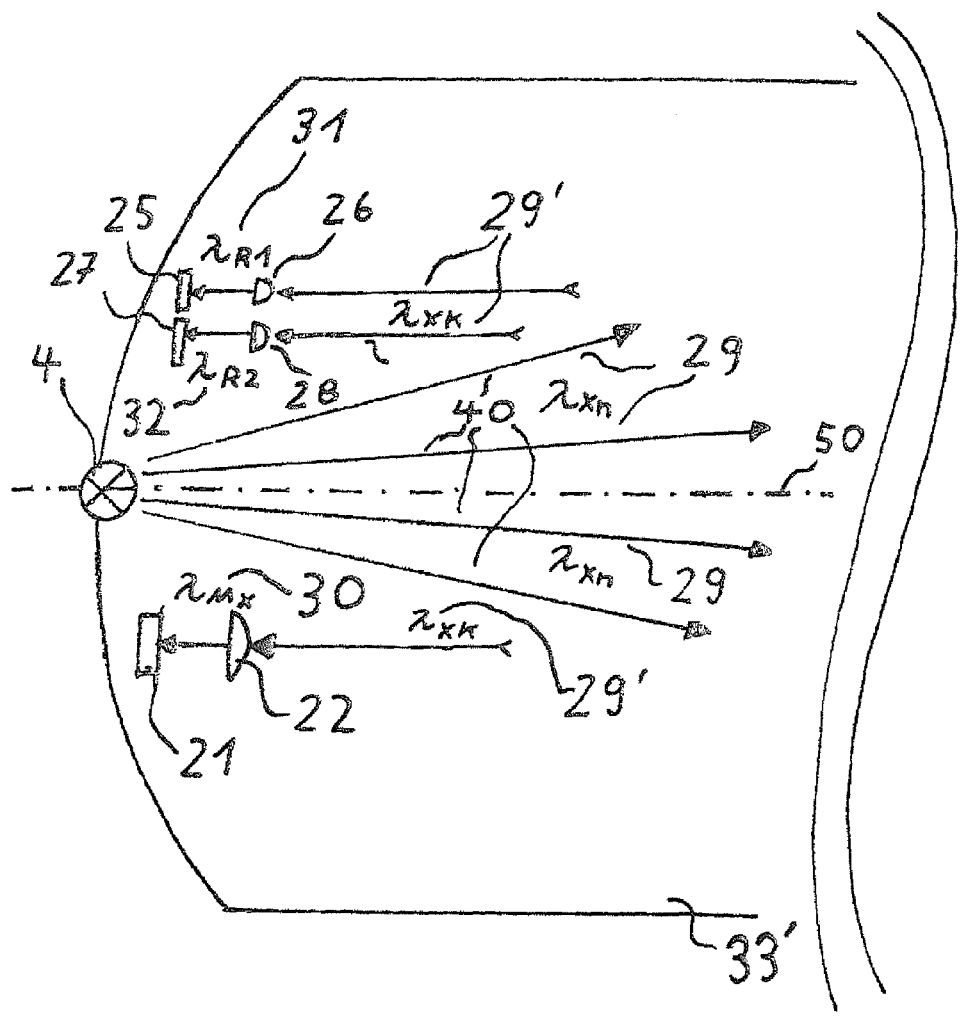

FIG. 2b shows a piece 33' of the measuring cuvette 33 according to FIG. 2a. Identical components in FIG. 2a and in FIG. 2b are designated by the same reference numbers as in FIG. 2a.

The piece 33' shown shows the metrological elements arranged on one side of the measuring cuvette 33 (FIG. 2a) (radiation source 4, measuring detector 21, measurement wavelength filter element 22, first reference detector 25, first reference wavelength filter element 26, second reference detector 27, and second reference wavelength filter element 28).

The radiation source 4 emits light as an essentially inhomogeneous light bundle 40 along an optical axis 30 in an infrared wavelength range $\lambda_{Xn}$ 29 into the measuring cuvette 33 (FIG. 2a).

The light is reflected multiple times in the multireflection measuring cuvette 33 (FIG. 2a), absorbed by the target gas along the optical path length of the measuring cuvette 33 (FIG. 2a), and it reaches as IR light $\lambda_{Xk}$ 29' the measurement wavelength filter element 22 and the first reference wavelength filter element 26 and the second reference wavelength filter element 28.

The measurement wavelength filter element 22 transmits from the infrared wavelength range $\lambda_{Xk}$ 29' only a component of the light in the range of the IR measurement wavelength $\lambda_{Mx}$ 30 to the measuring detector 21.

The first reference wavelength filter element 26 transmits from the infrared wavelength range $\lambda_{Xk}$ 29' only a component of the light in the range of the first IR reference wavelength $\lambda_{Rx1}$ 31 to the first reference detector 25.

The second reference wavelength filter element 28 transmits from the infrared wavelength range $\lambda_{Xk}$ 29' only a component of the light in the range of the second IR reference wavelength $\lambda_{Rx2}$ 32 to the second reference detector 27.

The measuring detector 22 and the first and second reference detectors 25, 27 are connected to the operating and analyzing unit 8 (FIG. 1a), so that the signals of the measuring detector 22 and of the reference detectors 25, 27 can be analyzed in the operating and analyzing unit 8 (FIG. 1a) in order to determine a target gas concentration with compensation of the effect of the moisture present in the target gas.

Figure 3:
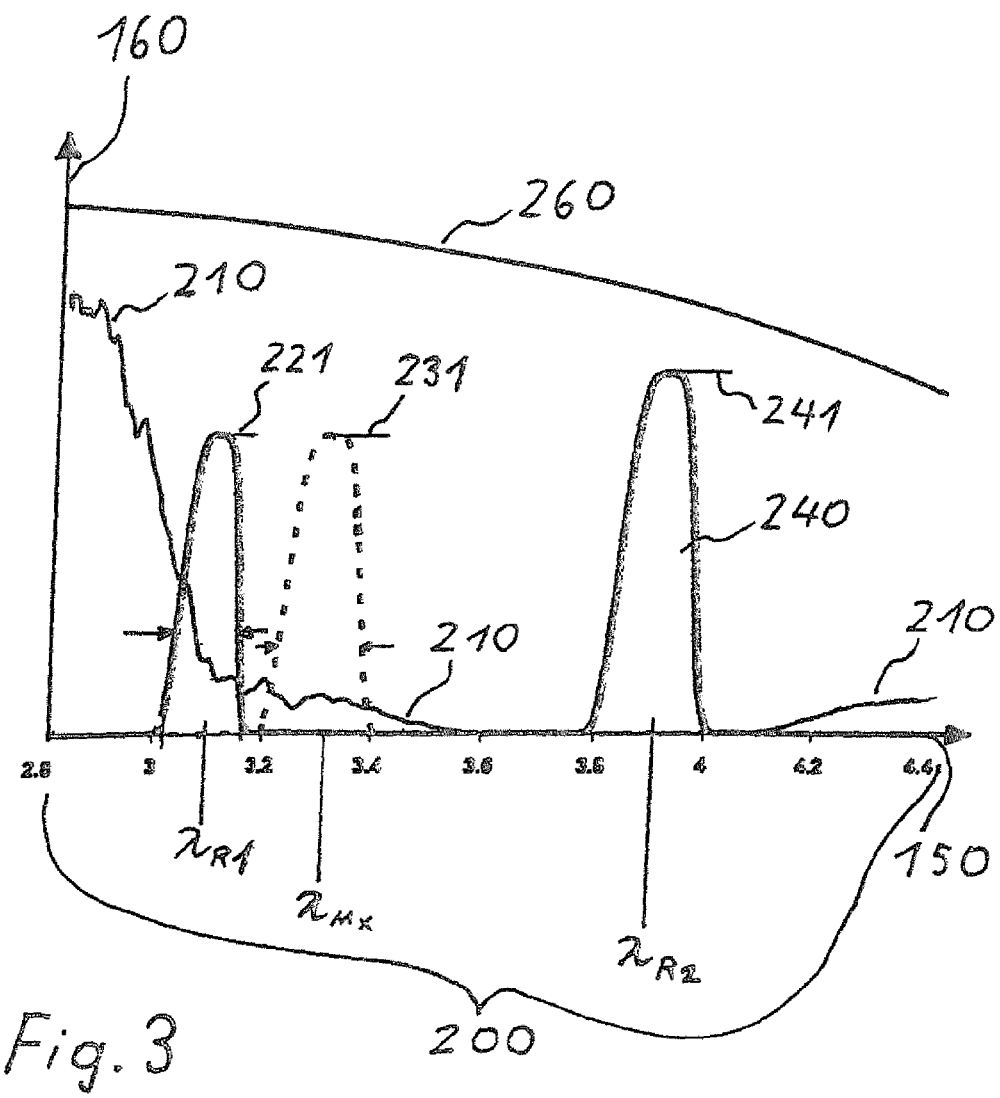
FIG. 3 is a spectral representation of the wavelengths of the measurement arrangement used in accordance with FIGS. 1a, 1b, 2a, 2b.

FIG. 3 shows a view of the measurement wavelengths used, of the reference wavelengths of the measurement arrangement 1 according to FIGS. 1a, 1b and of the measurement arrangement 100 according to FIGS. 2a, 2b.

A wavelength range 200 from 2,800 nm to 4,400 nm is shown on a linear scale on the abscissa (X axis) 150.

An absorption 210 of water and/or moisture from the measurement environment 6 (FIG. 1a, FIG. 2a), a transmission 220 of the first reference wavelength filter element 24 (FIG. 1a, FIG. 1b) and of the first reference wavelength filter element 26 (FIG. 2a, FIG. 2b) at the first reference wavelength, a transmission 240 of the first reference wavelength filter element 24 (FIG. 1a, FIG. 1b) and of the second reference wavelength filter element 28 (FIG. 2a, FIG. 2b) at the second reference wavelength, a transmission 230, drawn in broken line, of the first measurement wavelength filter element 22 (FIG. 1a, FIG. 1b, FIG. 2a, FIG. 2b) at the measurement wavelength, as well as the emission 260 of the radiation source 4 (FIGS. 1a, 1b, 1c, 1d) are shown over this wavelength range 200 on an ordinate (Y axis) 160.

The transmissions 220, 230, 240 are represented in this FIG. 3 without an effect of an absorption by the target gas in the wavelength range 200.

The transmission 220 is shown with a maximum of the transmission 221 at the reference wavelength $\lambda_{Rx1}$ 31 of 3,100 nm.

The transmission 240 is shown with a maximum of the transmission 241 at the reference wavelength $\lambda_{Rx2}$ 32 of 3,900 nm. The transmission 230 is shown with a maximum of the transmission 231 at the measurement wavelength $\lambda_{Mx}$ 30 of 3,300 nm. Furthermore, the respective transmission wavelength with the corresponding bandwidth is shown in a simplified form in and at the transmissions 220, 230, 240 shown according to this FIG. 3.

The transmission 220 at the first reference wavelength $\lambda_{Rx1}$ 31 has a bandwidth 222 of about 90 nm symmetrically in respect to the maximum 221 at the first wavelength $\lambda_{Rx1}$ 31. The transmission 240 at the second reference wavelength $\lambda_{Rx2}$ 32 has a bandwidth 242 of about 120 nm symmetrically in respect to the maximum 241 at the second reference wavelength $\lambda_{Rx2}$ 32. The transmission 230 at the measurement wavelength $\lambda_{Mx}$ 30 has a bandwidth 232 of about 100 nm symmetrically in respect to the maximum 231 at the measurement wavelength $\lambda_{Mx}$ 30.

Both the drop of the curve describing the absorption 210 of water and moisture over the wavelength range 200 and the drop of the emission of the radiation source 4 (FIG. 1a, 1b) over the wavelength range 200 are taken into account in the selection of the bandwidths 222, 242 and of the maxima of the transmission 221, 241 of the first reference wavelength filter element 24 (FIG. 1a, 1b) at the reference wavelengths $\lambda_{Rx1}$, $\lambda_{Rx2}$, 31, 32 for a measurement arrangement 1 according to FIG. 1a and FIG. 1b in such a way that the same effect due to the absorption 210 of water and moisture is obtained summarily as a signal at the first reference detector 23 (FIG. 1a, FIG. 1b) as at the measuring detector 21 (FIG. 1a, FIG. 1b) in conjunction with the measurement wavelength filter element 22 (FIG. 2a, FIG. 2b).

Both the drop of the curve describing the absorption 210 of water and moisture over the wavelength range 200 and the drop of the curve describing the emission of the radiation source 4 (FIG. 2a, 2b) over the wavelength range 200 are taken into account in the selection of the bandwidths 222, 242 and of the maxima of the transmission 221, 241 of the reference wavelength filter elements 26, 28 (FIGS. 2a, 2b) at the reference wavelengths $\lambda_{Rx1}$, $\lambda_{Rx2}$ 31, 32 for a measurement arrangement 100 according to FIG. 2a and FIG. 2b in such a way that the same effect due to the absorption 210 of water and moisture is obtained summarily as a signal at the first and second reference detectors 25, 27 (FIG. 2a, FIG. 2b) as at the measuring detector 21 (FIG. 2a, FIG. 2b) in conjunction with the measurement wavelength filter element 22 (FIG. 2a, FIG. 2b).

While specific embodiments of the invention have been shown and described in detail to illustrate the application of the principles of the invention, it will be understood that the invention may be embodied otherwise without departing from such principles.

The invention claimed is:

1. A device for the optical detection of a target gas in gas mixtures, the device comprising:
   an operating and analyzing unit;
   a measuring cuvette comprising a multireflection measuring cuvette with optically reflecting surfaces on the inner walls and a gas inlet to exchange gases and gas mixtures with a measurement environment;
   a radiation source, which emits light into the measuring cuvette;
   a measuring detector provided at the measuring cuvette;
   a reference detector unit provided at the measuring cuvette, wherein the measuring detector and the reference detector unit detect the light of the radiation source and produce electrical signals, which correspond to the intensity of the detected light;
   an optical band pass filter element, designed to transmit light of a measurement wavelength, arranged in front of the measuring detector; and
   an optical double band pass filter unit, designed to transmit light of a first reference wavelength and light of a second reference wavelength, arranged in front of the reference detector unit, wherein:
   the operating and analyzing operates the radiation source and receives the electrical signals of the measuring detector and of the reference detector unit;
   the operating and analyzing unit determines a target gas concentration with compensation of the effect of moisture present based on a determination of a moisture effect signal reduction in each of the signals belonging to the measurement wavelength and the first reference wavelength and the second reference wavelength.

2. A device in accordance with claim 1, wherein:
   the radiation source to emits light in the infrared wavelength range; and
   the measurement wavelength, the first reference wavelength and the second reference wavelength are in the infrared optical wavelength range.

3. A device in accordance with claim 1, wherein the light emitted by the radiation source reaches the measuring detector and the reference detector unit after an at least one-time reflection at the reflecting surfaces of the measuring cuvette.

4. A device in accordance with claim 1, wherein:
   the reference detector unit is designed as a reference detector and;
   the optical double band pass filter unit is designed as a double band pass filter element, which transmits light of the first reference wavelength and light of the second reference wavelength.

5. A device in accordance with claim 1, wherein:
   the reference detector unit has a first reference detector and a second reference detector;
   the optical double band pass filter unit has a first reference wavelength filter element and a second reference wavelength filter element;
   the first reference wavelength filter element transmits light in the range of the first reference wavelength to the first reference detector; and
   the second reference wavelength filter element transmits light in the range of the second reference wavelength to the second reference detector.

6. A device in accordance with claim 1, wherein at least one of the optical band pass filter element and the double band pass filter unit and the double band pass filter element and the first reference wavelength filter element and the second reference wavelength filter element are designed as an optical interference filter or a diffractive optical element.

7. A device in accordance with claim 1, further comprising:
   temperature sensors to detect temperatures of the wall of the measuring cuvette, of the measuring detector and of the reference detector unit.

8. A device in accordance with claim 1, further comprising:
   heating elements to temper the wall of at least one of the measuring cuvette, the measuring detector and the reference detector unit.

9. A device in accordance with claim 1, wherein the operating and analyzing unit is at least partly structurally separate from the measuring cuvette.

10. A device in accordance with claim 1, wherein the radiation source, the measuring detector and the reference detector unit are arranged on the same side in the measuring cuvette.

11. A device in accordance with claim 1, further comprising:
    a protective element, which is designed to prevent at least one of the transfer of contaminants from the measurement environment into the measuring cuvette and the transfer of quantities of energy from the measuring cuvette into the measurement environment, is arranged at the gas inlet towards the measurement environment.

12. A device in accordance with claim 1, wherein the device is arranged at least partly in a housing, wherein the housing has an explosion-proof design, so that no transfer of energy and no flashover of sparks from the housing into the measurement environment can take place.

13. A device in accordance with claim 1, wherein the measurement wavelength has a wavelength of 3,300 nm.

14. A device in accordance with claim 1, wherein the first reference wavelength has a wavelength of 3,100 nm.

15. A device in accordance with claim 1, wherein the second reference wavelength has a wavelength of 3,900 nm.

16. A device in accordance with claim 1, wherein the optical band pass filter element transmits light in the wavelength range of 3,200 nm to 3,500 nm to the measuring detector.

17. A device in accordance with claim 1, wherein the optical double band pass filter unit transmits light in the wavelength range of 3,000 nm to 3,200 nm and light in the wavelength range of 3,800 nm to 4,000 nm to the reference detector unit.

18. A device in accordance with claim 1, wherein the radiation source emits light in the infrared range of 2,000 nm to 5,000 nm.

19. A device in accordance with claim 1, wherein a filter element, which is designed to focus light emitted by the radiation source and/or to transmit light in a wavelength range of 3,000 nm to 4,000 nm, is arranged in front of the radiation source.

20. A device for the optical detection of a target gas in gas mixtures, the device comprising:
    an operating and analyzing unit;
    a measuring cuvette comprising a multireflection measuring cuvette with optically reflecting surfaces on the inner walls and a gas inlet to exchange gases and gas mixtures with a measurement environment;
    a radiation source, which emits light into the measuring cuvette;
    a measuring detector provided at the measuring cuvette;
    a reference detector unit provided at the measuring cuvette, wherein the measuring detector and the reference detector unit detect the light of the radiation source and produce electrical signals, which correspond to the intensity of the detected light;

an optical band pass filter element, designed to transmit light of a measurement wavelength, arranged in front of the measuring detector; and an optical double band pass filter unit, designed to transmit light of a first reference wavelength and light of a second reference wavelength, arranged in front of the reference detector unit, wherein the operating and analyzing unit is designed to operate the radiation source and to detect the electric signals of the measuring detector and of the reference detector unit, wherein the operating and analyzing unit is designed to compensate the effect of the atmospheric humidity from the signal belonging to the first reference wavelength, from the signal belonging to the second reference wavelength and from the signal belonging to the measurement wavelength, including the spectral measuring sensitivity characteristic of the measuring detector and including the spectral measuring sensitivity characteristic of the reference detector unit and to determine a target gas concentration.

* * * * *